United States Patent [19]

Fagelman

[11] 4,214,870

[45] Jul. 29, 1980

[54] DENTAL CLAMP

[76] Inventor: Jacob Fagelman, 1022 E. 23rd St., Brooklyn, N.Y. 11210

[21] Appl. No.: 956,694

[22] Filed: Nov. 1, 1978

[51] Int. Cl.³ .......................... A61C 5/12; A61F 5/04
[52] U.S. Cl. ............................... 433/40; 128/92 EA; 433/162
[58] Field of Search ............... 32/63; 128/92 EA, 346

[56] References Cited

U.S. PATENT DOCUMENTS

| 774,816 | 11/1904 | Babcock | 32/63 |
| 819,137 | 5/1906 | Herman | 32/63 |
| 1,151,253 | 8/1915 | Emerson | 32/63 |
| 2,253,132 | 8/1941 | Malson | 32/63 |
| 2,583,896 | 1/1952 | Siebrandt | 128/92 EA |
| 2,645,014 | 7/1953 | Mathison | 32/63 |
| 3,423,835 | 1/1969 | Mattern | 32/63 |
| 3,482,315 | 12/1969 | Tofflemire | 32/63 |
| 3,628,249 | 12/1971 | Wurl | 32/63 |
| 3,896,553 | 7/1975 | Fagelman | 32/63 |

Primary Examiner—Russell R. Kinsey
Assistant Examiner—Michael J. Foycik, Jr.
Attorney, Agent, or Firm—Leo C. Krazinski

[57] ABSTRACT

A dental clamp for maintaining steady pressure on a matrix strip of non-corrosive, flexible metal used to insert a Class III and/or a Class IV restoration to a tooth.

2 Claims, 7 Drawing Figures

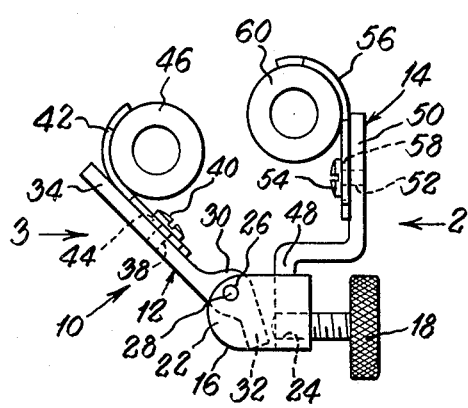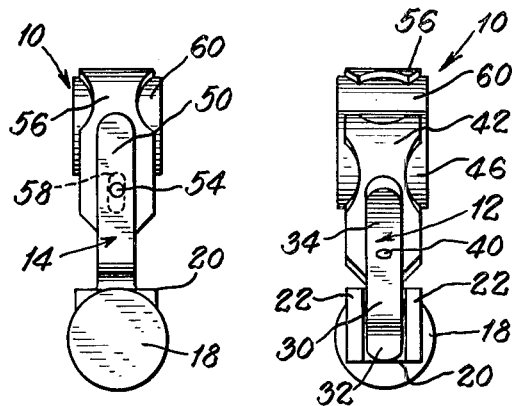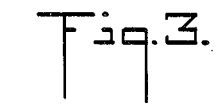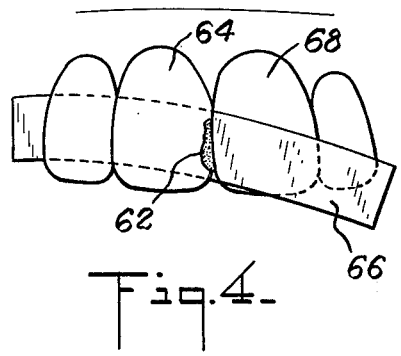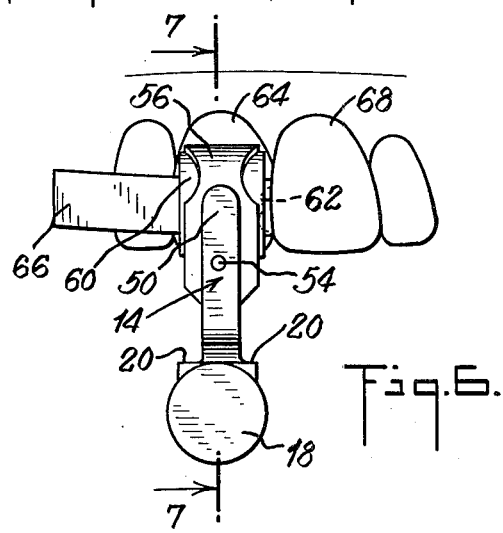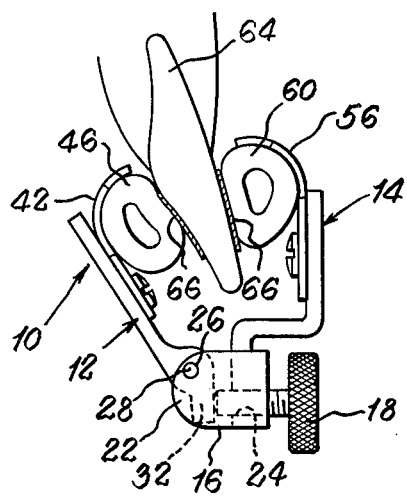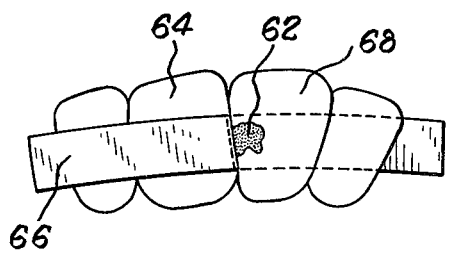

DENTAL CLAMP

BACKGROUND OF THE INVENTION

1. Field of the Invention

The present invention relates to dental instruments and, more particularly, to an improved dental clamp for removably securing a matrix to a tooth after a filling material had been added to a cavity of the tooth.

As far as applicant is aware, after filling material has been added to a tooth cavity, it is customary for the dentist to manually hold the matrix in position for a predetermined interval of time for the filling material to set. This is tedious, time consuming to the dentist who must maintain a fairly constant pressure on the matrix. As to prior art, applicant's U.S. Pat. No. 3,896,553 of July 7, 1975 is noted for clamping a dental instrument to a tooth.

Summary of the Invention

Accordingly, an object of the present invention is to provide an improved dental clamp.

Another object is to provide an improved metallic matrix strip of sufficient strength, yet flexible, which remains in proper contour upon application of substantial pressure.

Still another object is to provide an improved dental clamp for removably securing said matrix strip in position following application of filling material to a tooth cavity.

Yet another object is to provide such a dental clamp that is simple, practical and economical in construction, and is reliable and efficient in operation.

Other and further objects will be obvious upon an understanding of the illustrative embodiment about to be described, or will be indicated in the appended claims and various advantages not referred to herein will occur to one skilled in the art upon employment of the invention in practice.

BRIEF DESCRIPTION OF THE DRAWING

A preferred embodiment of the invention has been chosen for purposes of illustration and description and is shown in the accompanying drawing, forming a part of the specification, wherein:

FIG. 1 is a side elevational view of an improved dental clamp embodying the present invention.

FIG. 2 is an end elevational view of the clamp looking in the direction of the arrow 2 of FIG. 1.

FIG. 3 is an end elevational view of the clamp looking in the direction of the arrow 3 of FIG. 1.

FIG. 4 is a labial elevational view showing initial placement of a matrix strip around a tooth cavity.

FIG. 5 is a lingual elevational view, opposite to that of FIG. 4, showing initial placement of a matrix strip around a tooth cavity.

FIG. 6 is a labial elevational view showing clamp securing matrix strip to a tooth after the matrix strip has been placed in final position for pressing the filling material within the tooth cavity.

FIG. 7 is a vertical sectional view taken on line 7—7, in the direction of the arrows, of FIG. 6 showing the flexible inserts of the clamp arms pressed against the matrix strip surrounding the filling material of the tooth cavity.

DESCRIPTION OF PREFERRED EMBODIMENT

Referring now to the drawing, particularly to FIGS. 1, 2 and 3, there is shown a dental clamp 10 comprising two opposing arms 12 and 14, a U shaped bracket 16 for supporting said arms and a threaded screw 18 mounted upon said bracket for adjusting the relative positions of said arms. Bracket 16 is formed with a webb 20 and two parallel flanges 22 in which the webb 20 has a threaded opening 24 for the screw 18 and the flanges 22 have opposed openings 26 for a pin 28. Arm 12 has a sleeve 30 intermediate its ends which sleeve is pivotally mounted on the pin 28 with the lower portion 32 of arm 12 being offset from the upper portion 34 thereof. As is evident in FIG. 1, the position of the lower portion 32 is determined by that of screw 18. The upper portion 34 has a threaded opening 38 for a screw 40 for adjustably securing to the arm 12 a finger 42 having a slot 44 formed adjacent its lower end for the screw 40 and at its arcuate upper end a cylindrical, hollow element 46 rigidly secured thereto. Preferably the hollow element 46 is of flexible material as rubber. Arm 14 has its lower portion 48 rigidly secured to the webb 20 and has its upper portion 50 offset at substantially a right angle from its lower portion 48. As in arm 12, the upper portion 50 has a threaded opening 52 for a screw 54 for adjustably securing to the arm 14 a finger 56 having a slot 58 formed adjacent its lower end for the screw 54 and at its arcuate upper end a cylindrical hollow element 60, preferably of rubber, rigidly secured thereto. The clamping action of the clamp is readily evident in that, as the screw 18 is turned clockwise, the arm 12 approaches arm 14 to reduce the space between flexible elements 46 and 60 and, as the screw 18 is turned counterclockwise, the arms 12 and 14 are retracted from each other.

In use of the dental clamp 10, and referring to FIGS. 4 to 7, inclusive, filling material 62 is first added to the tooth cavity in any suitable manner, preferably as indicated in my U.S. Pat. No. 3,896,553. It may be mentioned that in the use of clamp 10 one is concerned particularly in connection with Class III and Class IV tooth restorations. In Class III the cavity is between the anterior teeth, upper or lower, mesial or distal, that is, the front six teeth of the upper or lower portion of the jaw. In Class IV the cavity falls in the category of Class III plus a cavity found in a corner of a tooth.

Therefore, assuming a cavity of the Class III composite restoration, as seen in FIGS. 4, 5 and 6, and that the filling 62 has been properly added to tooth 64, it is necessary that the filling be compressed and accurately sealed. Unfortunately, many failures occur in Class III restorations because of faulty insertions of the filling material and lack of control of compression. It is to be noted that a new matrix strip has been designed for placing, compressing and properly contouring a Class III restoration. As seen in FIGS. 4–7, there is shown a rectangular matrix strip 66, about 0.001" in thickness, of stainless steel material, which has been annealed to eliminate "strip memory"; in that the strip 66 will readily contour to the shape of the tooth and will resist returning to its original form. The matrix strip 66 is slid between the teeth 64 and 68, as seen in FIGS. 4 and 5, so that the exterior portion of the filling material 62 is completely covered by an intermediate portion of the matrix strip 66. The ends of the matrix strip 66 are then lapped over the tooth 64 and manually held in position by one hand of the dentist while with the other hand the clamp is raised into position around the tooth 64 and matrix strip 66. Contouring and retention of the matrix strip 66 is obtained by the two hollow elements 46 and 60 and retention of the clamp 10 is obtained by the crescent shaped terminal portions of fingers 42 and 56, which grip the buccal and lingual sides of the tooth 64 near the gingival. Compression on the matrix strip 66 is effected by turning the screw 18 clockwise, whereby the hollow elements 46 and 60 grip the strip 66 and tooth 64 in the manner shown in FIG. 7. After a predetermined time interval of say about five minutes, the clamp 10 is released by rotating the screw 18 counterclockwise and withdrawing the clamp from the tooth, after which the matrix strip 66 is removed. It is to be noted that the fingers 42 and 56 are slotted so as to enable the dentist to adjust the positions of the hollow elements 46 and 60, respectively, in accordance with the dimensions of the teeth to be treated.

As various changes may be made in the form, construction and arrangement of the parts herein, without departing from the spirit and scope of the invention and without sacrificing any of its advantages, it is to be understood that all matters are to be interpreted as illustrative and not in any limiting sense.

What is claimed is:

1. A dental instrument for tooth restoration comprising, in combination, a clamp including a channel shaped bracket armed with a web and two flanges, a pair of spaced arms carried by said bracket, means for pivotally mounting one of said arms on said bracket, means for rigidly securing the other arm to said bracket, an upper portion and a lower portion on said one arm, said lower portion being offset from said upper portion, said one arm having an opening therethrough intermediate said portions, said pivotal means including a pin loosely disposed in said one arm opening and having its ends secured in said bracket flanges, a finger on each of said arms, means for longitudinally adjusting positions of said fingers along said arms, a resilient element at a free end of each of said fingers, and means for adjusting the relative position of said one arm with respect to the other arm, whereby said spaced resilient elements may be adjustably disposed for tooth restoration.

2. A dental instrument in accordance with claim 1, wherein said lower portion of said arm is pivotally disposed between said flanges of the bracket, said webb of said bracket has a threaded opening therethrough and said arm adjusting means includes a screw passing through said threaded webb opening and engaging said lower portion of said one arm.

* * * * *